US006932082B2

(12) United States Patent
Stein

(10) Patent No.: US 6,932,082 B2
(45) Date of Patent: Aug. 23, 2005

(54) SPACER OR ACTUATOR FOR INERTIAL REMOVAL OF THE NON-RESPIRABLE FRACTION OF MEDICINAL AEROSOLS

(75) Inventor: Stephen W. Stein, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/370,973

(22) Filed: Feb. 20, 2003

(65) Prior Publication Data

US 2003/0196654 A1 Oct. 23, 2003

Related U.S. Application Data

(60) Provisional application No. 60/373,945, filed on Apr. 19, 2002.

(51) Int. Cl.$^{7}$ .............................................. A61M 11/00

(52) U.S. Cl. ............................ 128/200.22; 128/203.15

(58) Field of Search ...................... 128/200.22, 203.12, 128/203.15, 203.21

(56) References Cited

U.S. PATENT DOCUMENTS 506,368 A * 10/1893 Hoell .................... 128/200.22
1,263,079 A * 4/1918 Leon .......................... 239/338
1,853,242 A * 4/1932 Sliter .................... 128/200.22
2,381,558 A * 8/1945 Robinson .................... 239/338
3,038,532 A * 6/1962 Eisenkraft ................ 239/102.2
3,362,405 A * 1/1968 Hazel .................... 128/203.15
4,069,819 A 1/1978 Valentini et al.
4,228,795 A * 10/1980 Babington ............. 128/200.22
4,338,931 A 7/1982 Cavazza
5,170,782 A 12/1992 Kocinski
5,301,666 A 4/1994 Lerk et al.
5,309,900 A 5/1994 Knoch et al.
5,458,135 A 10/1995 Patton et al.
5,476,093 A 12/1995 Lankinen
5,596,982 A 1/1997 Blaha-Schnabel
5,676,130 A 10/1997 Gupte et al.
5,685,291 A 11/1997 Marsh
5,881,719 A 3/1999 Gottenauer et al.
6,073,629 A 6/2000 Hardy et al.
6,270,545 B1 8/2001 Lee et al.

FOREIGN PATENT DOCUMENTS

WO WO 88/03419 5/1988
WO WO 92/04066 3/1992
WO WO 98/26827 6/1998
WO WO 01/00262 1/2001
WO WO 01/60341 8/2001
WO WO 02/07805 1/2002

* cited by examiner

*Primary Examiner*—Aaron J. Lewis
(74) *Attorney, Agent, or Firm*—Cheree Haswell Johnson

(57) ABSTRACT

The invention comprises a medicinal inhaler spacer or actuator comprising a chamber having a proximal end closed by a proximal plate, a tangentially aligned inlet on the proximal end of the chamber, a tapered distal end, and an outlet extending through the proximal plate into and communicating with the chamber. Spacers of the present invention may be used to increase the respirable fraction of a medicinal aerosol inhaler. The invention also comprises medicinal aerosol inhalers and methods of delivering drug to the lung of a mammal employing these spacers.

2 Claims, 2 Drawing Sheets

150
120
100
140
132
110
130
134

SPACER OR ACTUATOR FOR INERTIAL REMOVAL OF THE NON-RESPIRABLE FRACTION OF MEDICINAL AEROSOLS

This application claims the benefit of earlier filed provisional application 60/373,945, filed Apr. 19, 2002.

The present invention relates to a spacer or actuator for inertial removal of the non-respirable fraction of medicinal aerosols. The present invention also relates to medicinal aerosol inhalers employing a spacer or actuator for inertial removal of the non-respirable fraction of the medicinal aerosol.

BACKGROUND OF THE INVENTION

Medicinal aerosol inhalers are commonly used to treat a number of medical conditions. It is well known that medicinal aerosols, whether they originate from a metered dose inhaler (MDI), dry powder inhaler (DPI), or a nebulizer, consist of a distribution of particles with varying sizes. For a particle to be considered respirable, meaning it will have a high probability of depositing in the lung upon inhalation, it should have an aerodynamic diameter of less than about 4.7 micrometers. Larger, non-respirable particles can be deposited in a patient's mouth and/or throat, which can lead to undesirable effects. Mouth and/or throat deposition can lead to a displeasing taste, as well as potentially causing side effects related to drug dosing by a non-inhalation route. It is thus desirable to provide an aerosol dose to a patient that consists primarily or entirely of respirable particles, that is, a dose that has a high respirable fraction.

In the development and manufacture of medicinal aerosol formulations, however, there are many factors that need to be taken into consideration, for example, drug solubility and/or stability in a suitable medium, the ability to prepare small particles, and the necessary dosage. Oftentimes, it is not possible or practical to make a medicinal aerosol where all of the particles delivered by a conventional device are respirable. A number of efforts have been made to develop spacers or actuators that provide either a longer or more tortuous path between the formulation reservoir and the patient to either remove non-respirable material or disperse larger aggregates into smaller particles. Medicinal inhaler spacers have incorporated additional distance and/or various configurations of baffles as a method for removal of non-respirable particles (U.S. Pat. No. 5,676,130, Gupte et al.; WO 92/04066, Bisgaard). Rotational motion of an airflow stream has also been proposed (U.S. Pat. No. 6,073,629, Hardy et al.) and in particular airflows described as cyclonic wherein the airflow travels from inlet to outlet by spiraling in one direction along a central axis (U.S. Pat. No. 5,476,093,Lankinen; WO 01/00262, Hamer et al.).

SUMMARY OF THE INVENTION

It has now been found that certain types of cyclone spacers can be a highly effective, compact, and robust way to increase the respirable fraction of a medicinal aerosol. Non-respirable particles that enter the inlet of the spacer are preferentially removed from the airstream through inertial deposition onto the interior surfaces of the spacer, thereby increasing the respirable fraction of the medicinal aerosol.

The present invention provides a medicinal inhaler spacer comprising a chamber having a proximal end closed by a proximal plate, a tangentially aligned inlet on the proximal end of the chamber, a tapered distal end, and an outlet extending through the proximal plate into and communicating with the chamber.

The present invention further comprises a medicinal aerosol inhaler comprising a medicinal inhaler spacer of the invention where the inlet of the spacer is in fluid communication with an aerosol generation system and the outlet of the spacer is in fluid communication with a mouthpiece.

The invention also further comprises a method of delivering a medicinal aerosol to the lung of a mammal using this medicinal inhaler.

In another embodiment the invention comprises a medicinal aerosol inhaler comprising an aerosol generation system, a cyclone chamber, and a mouthpiece, wherein the inlet of the cyclone chamber is in fluid communication with the aerosol generation system and the outlet of the cyclone chamber is in fluid communication with the mouthpiece. The cyclone chamber has a tapered distal end and an outlet extending through the proximal end.

BRIEF DESCRIPTION OF THE DRAWINGS

Preferred embodiments of the invention will now be described in greater detail below with reference to the attached drawings, wherein.

DETAILED DESCRIPTION OF THE INVENTION

Figure 1:
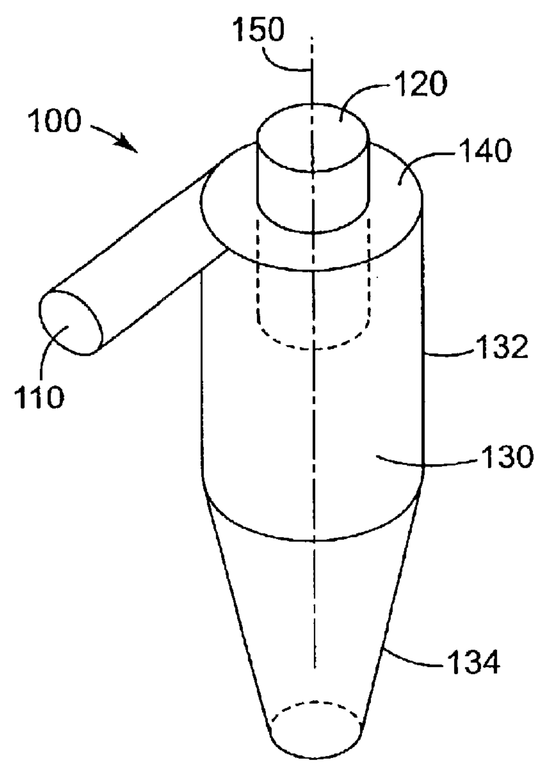
FIG. 1 is a perspective view of a medicinal inhaler spacer.

FIG. 1 shows a perspective view of a preferred embodiment of a medicinal inhaler spacer 100 of the present invention.

The spacer 100 comprises an inlet 110 that is located tangentially on a circumferential outer surface of a chamber 130. The inlet 110 adjoins the chamber 130 along the proximal end 132 of the chamber. As shown in FIG. 1 the inlet 110 is cylindrical, but it may also be rectangular, oval, tubular, or any like shape that will provide for an opening into the chamber 130 through which air may flow.

Figure 2:
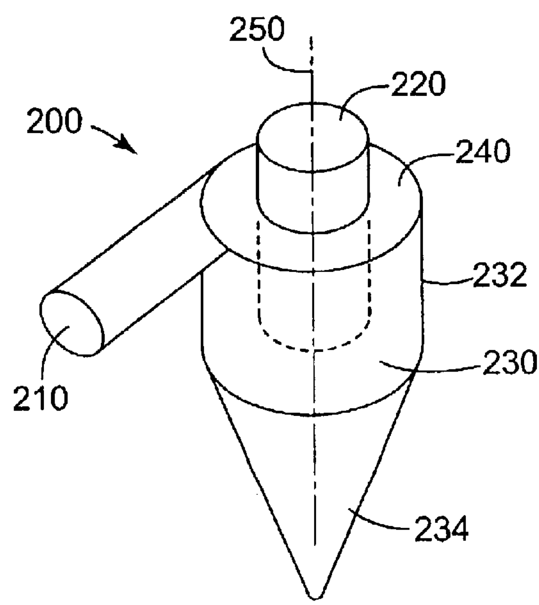
FIG. 2 is a perspective view of a medicinal inhaler spacer.

The chamber 130 preferably has rounded sides and the proximal end 132 of the chamber is more preferably in the shape of a cylinder that defines a central axis 150. The chamber 130 has a taper over its distal end 134, preferably in the form of a distally converging cylinder. As shown in FIG. 1 this distally converging cylinder may be closed at its distal end. Alternatively, as shown in FIG. 2, the distal end 234 of the chamber 230 tapers towards a point making the distal end of the chamber conical, as opposed to the truncated conical distal end shown in FIG. 1.

The proximal end 132 of the chamber is capped with a proximal plate 140. As shown in FIG. 1 the proximal plate 140 may be flat, but the intended function is to cap the proximal end of the chamber and so, for example, it may also be rounded or curved in shape. The proximal plate 140 may be a separate piece that is attached to the chamber 130 or it may be made integral with the chamber 130.

An outlet 120 extends through the proximal plate 140 and communicates with the interior of the chamber 130. In a preferred embodiment the outlet 120 extends into the chamber 130 to a level below the bottom of the inlet 110 opening. In another preferred embodiment the ratio of the distance of the outlet extension into the chamber to the length of the proximal end 132 of the chamber is between about 0.5 and 2.0, and more preferably between 0.75 and 1.5. As shown the outlet 120 is cylindrical in shape, but it may also be oval, tubular, rectangular, or any like shape that will provide for an opening into the chamber 130 through which air may flow.

The central axis 150 preferably passes through the outlet 120 where the outlet 120 passes through the proximal plate 140. In a more preferred embodiment the outlet 120 defines an outlet axis that is substantially coaxial with the central axis 150, and is most preferably coaxial with the central axis 150, as shown in FIG. 1.

Figure 3:
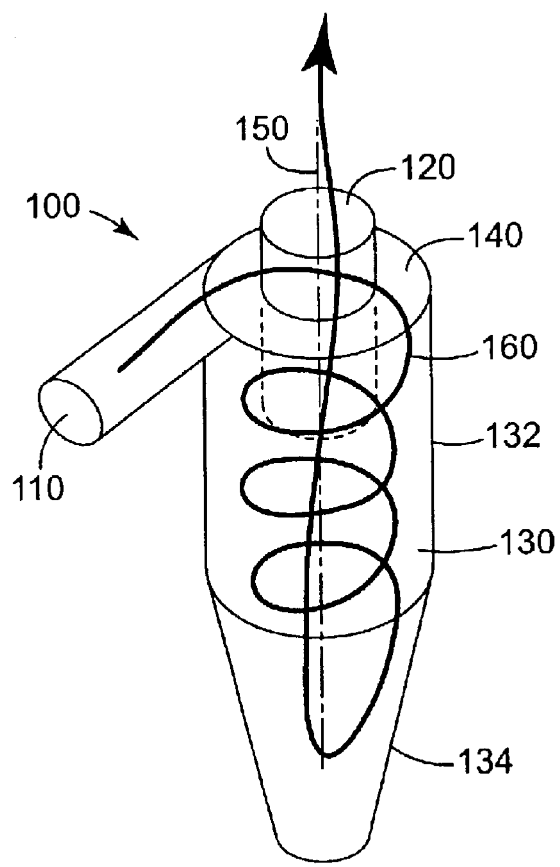
FIG. 3 is a perspective view of a medicinal inhaler spacer with a schematic diagram of an airflow pattern.

In use, an airstream flows into the inlet, passes through the chamber, and flows out of the outlet. The airflow passing through the chamber preferably undergoes rotational flow around the central axis 150, and more preferably undergoes rotational flow of more than 360 degrees around the central axis 150. The extension of the outlet into the chamber inhibits a direct linear airflow from inlet to outlet and aids in allowing the airstream to undergo multiple rotations, which leads to greater efficiency of removal of non-respirable particles. Although non-limiting to the scope of the invention, it is theorized that in this embodiment the airflow 160 enters the inlet 110, simultaneously rotates around the central axis 150 and translates distally in the chamber 130, until becoming constricted by the distal taper. After becoming constricted, the airflow 160 is then redirected along the central axis 150 and out of the outlet 120. The combination of the distal rotational motion along with the reversal of direction of the airflow caused by the constricting taper leads to efficient removal of non-respirable particles. This airflow pattern is shown schematically in FIG. 3.

The inlet 110 is defined on a circumferential outer surface of the chamber adjoining the proximal end 132 of the chamber, such that it is tangentially aligned with the proximal end 132 of the chamber. More preferably, the inlet 110 adjoins the proximal end 132 of the chamber where the proximal end 132 connects to the proximal plate 140. It should be understood that the inlet is preferably adapted to direct an inlet airflow in a substantially circumferential direction in the chamber and therefore allow for the creation of a rotational airflow and that this would include minor modifications in the position of the inlet in relation to the chamber In a preferred embodiment a particle collecting means, not shown, may be provided within or adjacent to the distal end of the chamber. Particles may, for example, be collected in the distal end of the chamber by adhesive means, such as a tape, glue, gel, or a high viscosity liquid. Particles may also be collected in or adjacent to the distal end of the chamber by mechanical means, such as one or more small openings in the distal part of the chamber 130 that allow particles to easily fall through the openings and into a collection reservoir adjacent to the distal end, the openings being sized so as to make it difficult for particles to pass from the collection reservoir back into the chamber. Collection of particles at the base of or adjacent to the distal end of the chamber allows repeated use of the spacer without need for cleaning or emptying, and prevents or limits re-entrainment of non-respirable particles into airflows generated by subsequent dosing.

In use, an airflow comprising an aerosol that passes through the inlet 110 into the chamber 130 will undergo centrifugal forces that can lead to solid or liquid particles of the aerosol impacting the surfaces of the chamber 130. In particular, larger particles have more inertia and a greater tendency to deviate from the airflow and are therefore more likely to impact on the chamber surfaces. It should be understood that one skilled in the art will appreciate that size and shape of the inlet 110, outlet 120, and chamber 130 can be adjusted to change the likelihood that particles of a given size will impact upon the chamber surface. In particular, the spacer can be sized such that for given parameters of airflow velocity and particle density, a "cut-off" size can be estimated. Particles larger than the "cut-off" size will be expected to impact the chamber surface and particles smaller than the "cut-off" size will be expected to pass through the chamber 130 and leave the outlet 110. Although theoretically scalable to any size, it will be appreciated that the height and width of the spacer should be of a size that is convenient for a patient to handle, and these dimensions will preferably be between 1 and 20 cm, and more preferably between 2 and 5 cm.

The present invention further comprises a medicinal aerosol inhaler comprising a medicinal inhaler spacer of the invention where the inlet of the spacer is in fluid communication with an aerosol generation system and the outlet of the spacer is in fluid communication with a mouthpiece. In a preferred embodiment the aerosol generation system comprises a pressurized aerosol canister, a dry powder generation system, or a nebulization system.

EXAMPLES

Particle Collection Testing

Particle collection characteristics were tested using a Model 160 Marple Miller Impactor (MMI) coupled with a USP throat (United States Pharmacopeia, USP 24 <601> Aerosols, Metered Dose Inhalers, and Dry Powder Inhalers, FIG. 4) and a volumetric flow rate of 60 L/min. Aerosol generation was provided by a Turbohaler® DPI (manufactured by Astra Pharmaceuticals), a commercially available dry powder delivery device. For all testing, the stage cups of the MMI were coated with a surfactant to prevent particle bounce and re-entrainment.

The outlet of the dry powder delivery device was connected to the inlet of the spacer and the outlet of the spacer was connected to the USP throat.

The amount of drug deposited in the spacers and in each individual component of the MMI apparatus was determined by rinsing the component with a measured volume of an appropriate solvent and subjecting the rinsate to standard HPLC analysis to determine concentration. Data that was returned from HPLC analysis was analyzed to determine the average amount of drug collected per delivered dose. The resulting mass values were then normalized to the fraction of delivered dose collected in each individual component of the testing assembly.

Using the individual component values, the amount of throat deposition, the respirable mass, and the respirable fraction was calculated for each device. Throat deposition is defined as the percent of the total delivered dose that deposits in the USP throat. Respirable mass is defined as the percentage of the total delivered dose that is measured to be smaller than the respirable limit of 4.7 micrometers in aerodynamic diameter. Respirable fraction is defined as the percentage of a delivered dose that reaches the entry of the throat and is smaller than the respirable limit. When using the MMI, respirable mass is collected in cups 2, 3, 4, and on the filter. Mass collected in the throat and cups 0 and 1 are considered non-respirable.

Example 1

A spacer of the general design depicted in FIG. 2 was constructed with the following dimensions: inlet port of diameter 1.0 cm; chamber inside diameter 4.0 cm; non-tapered end of chamber height 2.4 cm; tapered end of chamber height 4.8 cm with a taper angle of 22.6 degrees; outlet port diameter 2.0 cm with an extension of 2.0 cm into the chamber.

Particle collection characteristics were determined by attaching the spacer to a Turbohaler® and are shown in Table 1. The particle collection characteristics for a Turbohaler® connected directly to the USP throat are shown for comparison.

Example 2

A spacer of the general design depicted in FIG. 2 was constructed with the following dimensions: inlet port of diameter 0.75 cm; chamber inside diameter 3.0 cm; non-tapered end of chamber height 1.8 cm; tapered end of chamber height 3.6 cm with a taper angle of 22.6 degrees; outlet port diameter 1.5 cm with an extension of 1.5 cm into the chamber.

Particle collection characteristics were determined by attaching the spacer to a Turbohaler® and are shown in Table 1. The particle collection characteristics for a Turbohaler® connected directly to the USP throat are shown for comparison.

Example 3

A spacer of the general design depicted in FIG. 2 was constructed with the following dimensions: inlet port of diameter 0.5 cm; chamber inside diameter 2.0 cm; non-tapered end of chamber height 1.2 cm; tapered end of chamber height 2.4 cm with a taper angle of 22.6 degrees; outlet port diameter 1.0 cm with an extension of 1.0 cm into the chamber.

Particle collection characteristics were determined by attaching the spacer to a Turbohaler® and are shown in Table 1. The particle collection characteristics for a Turbohaler® connected directly to the USP throat are shown for comparison.

TABLE 1

| | Turbohaler ® | Example 1 | Example 2 | Example 3 |
|---|---|---|---|---|
| Throat Deposition (% of total) | 53.4 | 0.01 | 0.04 | 0.03 |
| Respirable Mass (% of total) | 39.5 | 24.1 | 10.8 | 8.5 |
| Respirable Fraction (% of total inhaled) | 35.0 | 99.9 | 98.7 | 99.7 |

Example 4

A spacer of the general design depicted in FIG. 1 was constructed with the following dimensions: inlet port of diameter 1.02 cm; chamber inside diameter 5.08 cm; non-tapered end of chamber height 1.27 cm; tapered end of chamber height 1.27 cm with a taper angle of 56.3 degrees; cyclone body base diameter of 1.27 cm; outlet port diameter 2.03 cm with an extension of 1.78 cm into the chamber.

Particle collection characteristics were determined by attaching the spacer to a Turbohaler® and are shown in Table 2. The particle collection characteristics for a Turbohaler® connected directly to the USP throat are shown for comparison.

Example 5

A spacer of the general design depicted in FIG. 1 was constructed with the following dimensions: inlet port of diameter 1.02 cm; chamber inside diameter 5.08 cm; non-tapered end of chamber height 1.27 cm; tapered end of chamber height 1.27 cm with a taper angle of 56.3 degrees; cyclone body base diameter of 1.27 cm; outlet port diameter 2.03 cm with an extension of 1.27 cm into the chamber.

Particle collection characteristics were determined by attaching the spacer to a Turbohaler® and are shown in Table 2. The particle collection characteristics for a Turbohaler® connected directly to the USP throat are shown for comparison.

TABLE 2

| | Turbohaler ® | Example 4 | Example 5 |
|---|---|---|---|
| Throat Deposition (% of total) | 53.4 | 0.1 | 0.2 |
| Respirable Mass (% of total) | 39.5 | 25.8 | 23.5 |
| Respirable Fraction (% of total inhaled) | 35.0 | 99.6 | 99.0 |

I claim:

1. A medicinal aerosol inhaler comprising:

an aerosol generation system;

a medicinal inhaler spacer wherein a chamber having a proximal end is closed by a proximal plate, a tangentially aligned inlet on the proximal end of the chamber, a tapered distal end, and an outlet extending through the proximal plate into and communicating with the chamber; and a mouthpiece, wherein the inlet of the spacer is in fluid communication with the aerosol generation system and the outlet of the spacer is in fluid communication with the mouthpiece, wherein the aerosol produced by the aerosol generation system passes through the inlet and into the chamber.

2. A medicinal aerosol inhaler comprising:

an aerosol generation system;

a medicinal inhaler spacer wherein a chamber having a proximal end is closed by a proximal plate, a tangentially aligned inlet on the proximal end of the chamber, a tapered distal end, and an outlet extending through the proximal plate into and communicating with the chamber, wherein the chamber has only one inlet and one outlet; and a mouthpiece, wherein the inlet of the spacer is in fluid communication with the aerosol generation system and the outlet of the spacer is in fluid communication with the mouthpiece, wherein the aerosol produced by the aerosol generation system passes through the inlet and into the chamber.

* * * * *